(12) United States Patent
Pluznick et al.

(10) Patent No.: US 11,592,445 B2
(45) Date of Patent: Feb. 28, 2023

(54) OLFR90 SPECIFICITY AND METHODS OF DETECTION

(71) Applicant: THE JOHNS HOPKINS UNIVERSITY, Baltimore, MD (US)

(72) Inventors: Jennifer Pluznick, Lutherville-Timonium, MD (US); Kieren A. Marr, Baltimore, MD (US); Victoria H. Kuhns, Catonsville, MD (US)

(73) Assignee: The Johns Hopkins University, Baltimore, MD (US)

( * ) Notice: Subject to any disclaimer, the term of this patent is extended or adjusted under 35 U.S.C. 154(b) by 1193 days.

(21) Appl. No.: 16/139,438

(22) Filed: Sep. 24, 2018

(65) Prior Publication Data

US 2019/0064161 A1    Feb. 28, 2019

Related U.S. Application Data

(63) Continuation-in-part of application No. PCT/US2017/024974, filed on Mar. 30, 2017.

(60) Provisional application No. 62/315,063, filed on Mar. 30, 2016.

(51) Int. Cl.

| | | |
|---|---|---|
| *G01N 33/566* | (2006.01) | |
| *A61K 31/015* | (2006.01) | |
| *G01N 31/22* | (2006.01) | |
| *G01N 33/53* | (2006.01) | |
| *G01N 33/00* | (2006.01) | |
| *A61K 31/045* | (2006.01) | |
| *A61K 31/11* | (2006.01) | |
| *A61K 31/121* | (2006.01) | |
| *A61K 31/277* | (2006.01) | |
| *A61K 31/341* | (2006.01) | |
| *A61K 31/39* | (2006.01) | |

(52) U.S. Cl.
CPC ......... *G01N 33/566* (2013.01); *A61K 31/015* (2013.01); *A61K 31/045* (2013.01); *A61K 31/11* (2013.01); *A61K 31/121* (2013.01); *A61K 31/277* (2013.01); *A61K 31/341* (2013.01); *A61K 31/39* (2013.01); *G01N 31/22* (2013.01); *G01N 33/0047* (2013.01); *G01N 33/5308* (2013.01); *G01N 2333/37* (2013.01); *G01N 2333/705* (2013.01); *G01N 2333/90241* (2013.01)

(58) Field of Classification Search
CPC ........................... G01N 33/566; A61K 31/015
See application file for complete search history.

(56) References Cited

U.S. PATENT DOCUMENTS

| | | | |
|---|---|---|---|
| 5,399,363 | A | 3/1995 | Liversidge et al. |
| 5,466,468 | A | 11/1995 | Schneider et al. |
| 5,543,158 | A | 8/1996 | Gref et al. |
| 5,580,579 | A | 12/1996 | Ruddy et al. |
| 5,629,001 | A | 5/1997 | Michael et al. |
| 5,641,515 | A | 6/1997 | Ramtoola |
| 5,725,871 | A | 3/1998 | Illum |
| 5,756,353 | A | 5/1998 | Debs |
| 5,780,045 | A | 7/1998 | McQuinn et al. |
| 5,792,451 | A | 8/1998 | Sarubbi et al. |
| 5,804,212 | A | 9/1998 | Illum |
| 6,613,308 | B2 | 9/2003 | Bartus et al. |
| 6,737,514 | B1 | 5/2004 | Wang et al. |
| 8,609,083 | B1 | 12/2013 | Shapiro-Ilan et al. |
| 2013/0338034 | A1 | 12/2013 | Park |

FOREIGN PATENT DOCUMENTS

WO    2011/094208 A2    8/2011

OTHER PUBLICATIONS

Takenaga et al., 1998 Microparticle resins as a potential nasal drug delivery system for insulin., J Control Release 52:81-7.
Mathiowitz et al., 1997 Biologically erodable microspheres as potential oral drug delivery systems., Nature 386 (6623):410-4.
Kang, N, et al., "Olfactory receptors in non-chemosensory tissues" BMB Reports (2012) vol. 45, No. 11, pp. 612-622.
Kajiya, K., et al., "Molecular Bases of Odor Discrimination: Reconstitution of Olfactory Receptors that Recognize Overlapping Sets of Odorants" The Journal of Neuroscience, Aug. 15, 2001, 21(16):6018-6025.
Katada, S., et al., "Odorant response assays for a heterologously expressed olfactory receptor" Biochemical and Biophysical Research Communications 305 (2003) 964-969.
Ma, R., et al., "Store-operated Ca2+ channels in human glomerular mesangial cells" Am J Physiol Renal Physiol 278: F954-F961, 2000.
Peterlin, Z., et al., "The state of the art of odorant receptor deorphanization: A report from the orphanage" J. Gen. Physiol. vol. 143 No. 5 527-542, 2014.
Pluznick, J., et al., "Functional expression of the olfactory signaling system in the kidney" PNAS (2009) vol. 106, No. 6, pp. 2059-2064.

*Primary Examiner* — Yong S. Chong
(74) *Attorney, Agent, or Firm* — Fox Rothschild LLP (57) ABSTRACT

The present invention describes methods of using Olfr90 demonstrated to bind to fungal metabolites, including a metabolite known to be detected in patients with mold (e.g. *Aspergillus*) infections.

17 Claims, 6 Drawing Sheets

OLFR90 SPECIFICITY AND METHODS OF DETECTION

REFERENCE TO RELATED APPLICATIONS

This US CIP application claims the benefit of International Patent Application PCT/US2017/024974, filed Mar. 30, 2017 and U.S. Provisional Patent Application No. 62/315,063 filed on Mar. 30, 2016, which are hereby incorporated by reference for all purposes as if fully set forth herein.

STATEMENT OF GOVERNMENTAL INTEREST

This invention was made with government support under grant no. DK104454, awarded by the National Institutes of Health. The government has certain rights in the invention.

BACKGROUND OF THE INVENTION

Fungi are ubiquitous Eukaryotic organisms that are present in our environment. The organisms typically grow as single cell yeasts or multicellular molds, and some transition between morphologies depending on growth conditions. For the most part, these organisms were not evolved to cause severe disease in animals, but instead grow as saprophytes in the environment, well adapted in a commensal state with animals. Disease caused by molds has been increasingly recognized, especially as mammalian fitness levels and immune defenses have adapted to changing environments. Increasingly, invasive mold infections have been recognized in people who are immune compromised by genetic conditions, aging, other infections (e.g. HIV) and modern medicine (e.g. transplantation). Moreover, increasing evidence points to the role of these organisms as causes of environmental toxicities and industrial spoilage. An over-abundance of mold products—especially the organic metabolites that are secreted during the asexual reproduction phase—have been associated with food spoilage, industrial contaminations, and the medical syndrome characterized by respiratory complaints and generalized feelings of being unwell, frequently called "sick building syndrome". Over-exposure to molds has been associated with several allergic manifestations, including asthma and allergic sinusitis. For these reasons, there has been increasing need to identify the presence of molds in the environment, industrial products and animals, enabling improvements in environmental health and medicine.

Although molds are ubiquitous in the environment, they are relatively difficult to cultivate in laboratory synthetic media, limiting sensitivities of culture-based diagnostic methods for environmental monitoring and diagnosis of invasive infection. Currently, screening for mold growth using air-sampling is the gold standard for environmental screening, although these methods are laborious, insensitive, and do not specifically distinguish between innocuous molds and the ones that produce harmful products. Current efforts have turned towards identifying the actual harmful products—volatile organic compounds (VOCs)—by mass spectrometry, but these methods are also very laborious and complex. Food and product screening remains difficult, and contaminations continue to impact industry.

Diagnosing invasive mold infections in animals is also difficult, in part due to some of the same reasons. These organisms do not replicate by simple binary fission and alternative growth conditions are required in the laboratory. Also, it can be difficult to obtain adequate tissue samples from the most frequently involved site, i.e., the lungs, without inducing excessive morbidity. Adjunctive diagnostic tests have been developed and are in common use. These typically rely on identification of polysaccharides that are on the cell wall of most fungi, called galactomannan or beta D glucan, or identification of fungal nucleic acids. Detection of polysaccharides is limited by non-specificity, as many such organisms have these components. Development of diagnostic tests that detect nucleic acids, which has been more successfully employed for viral infections, has been more elusive for fungi, in part due to the complexities of harvesting nucleic acids from fungal cells, presence of multiple genomes within multicellular filamentous organisms, and unreliable 'release' of nucleic acids from local compartments (lung) into systemic circulation. While fungal metabolites (VOCs) are also present in respiratory fluids and airways of people who have a high probability of invasive mold pneumonia, methods to detect these compounds are complicated, requiring spectrophotometry.

Commercial needs exist to create fungal detection and diagnostic tests to enhance the safety of environments, industrial products such as foods, and to enhance methods to prevent and diagnose invasive fungal infections in animals.

SUMMARY OF THE INVENTION

The methods of the present inventions address these needs by creating detection methods based on the identification of Olfr90 ligands.

One embodiment of the present invention is a detection method comprising the following steps: providing a sample taken from a source to be tested for the presence of a Olfr90 ligand; providing an Olfr90, or a ligand binding part thereof; placing the sample in contact with Olfr90, or the ligand binding part thereof; and detecting the presence or absence of an Olfr90 ligand in the sample. An example of a human Olfr90 protein sequence may be found on the NCBI (National Center for Biotechnology Information) database having a NCBI Reference Sequence: NP_666688.2. The source may be air, plants, humans, water, food, soil, wall scrapings, blood, urine, or respiratory samples, for example. A sample comprising an Olfr90 ligand used in the present invention includes a fungus such as a single cell yeast, a mold, or an environmental fungal threat to plants such as Fusarium that produces a metabolite pentylfuran, a potential Olfr90 ligand. A sample comprising an Olfr90 ligand may also be a non-fungal organism, such as other Eukaryotic organisms (ex. algae, protozoa) or Prokaryotic organisms (ex. bacteria), that produce an Olfr90 ligand. The term "ligand binding part thereof" is defined as the region of Olfr90 capable of binding one or more Olfr90 ligands. Alternatively, the ligand binding part of Olfr90 may be thought of as a ligand binding domain. A ligand is an entity (chemical, peptide, nucleic acid, for example) that binds to a protein, such as Olfr90, most preferably at the ligand binding domain of the protein. Olfr90 may be a mammalian protein, preferably mouse, rat, pig, or human. It is preferred that an Olfr90, or the ligand binding part thereof, is attached to a reporter and an Olfr90 ligand is detected in a sample by the displacement of the reporter if a Olfr90 ligand is present in the sample and binds to Olfr90, or a functional part thereof. Alternatively, Olfr90, or the ligand binding part thereof, is expressed in Eukaryotic cells along with a firefly luciferase whose activity is dependent upon elevated [c-AMP] whereby the detection of an Olfr90 ligand occurs by binding of the Olfr90 ligand to the Olfr90, or the ligand binding part thereof, which elevates the concentration of [cAMP] leading to increased transcription of firefly luciferase if an Olfr90 ligand is present in the sample and binds to Olfr90 or the ligand binding part thereof. Alternatively, Olfr90, or the ligand binding part thereof, may be expressed in Eukaryotic cells and a CNG channel (preferably CNGA2) is expressed exogenously, whereby the detection of an Olfr90 ligand occurs by binding of Olfr90 ligand to Olfr90, or the ligand binding part thereof, which elevates the concentration of [cAMP] leading to increased cAMP binding to CNGA2 and a resulting calcium influx may be measured via a detector. Examples of suitable detectors are a calcium sensitive dye or a FLIPR assay. Other detectors used in the present invention include human visualization and electronic detectors that are connected to a computer enabling quantification of the amount of color or calcium influx, for example, produced during the methods of the present invention that are correlated to the amount of Olfr90 ligand in a sample. It is preferred in some of the detection methods of the present invention that an Olfr90, or the ligand binding part thereof, is provided and immobilized to a surface. Some detection methods of the present invention include the additional steps of incubating the sample with the ligand binding part of Olfr90 to form a mixture; and adding a labeled Olfr90 ligand. A suitable label is selected from the group consisting of a fluorescent tag, colorimetric tag, or absorbance tag. One preferred ligand binding part of Olfr90 is an aptamer representing the binding site of Olfr90 and the aptamer is labeled with a tag, a fluorophore, for example. An Olfr90, or the ligand binding part thereof, such as an aptamer is preferably attached to a surface such as a strip or a dip stick. The presence or absence of an Olfr90 ligand is detected in a sample may be determined by the amount of fluorophore that remains bound to the aptamer. It is preferable that an Olfr90 ligand is a fungal metabolite selected from the group consisting of 1-Octen-3-ol, 2-Pentylfuran, 1-Octen-3-one, 1,3-Dimethoxybenzene, Linalool, Benzyl Cyanide, 2-Octen-1-ol, 3-Octanol, 2-Octanone, 3-Octanone, 2-Octen-1-al, 1-octanol, 2,5-dimethylfuran or combinations thereof. Other examples of Olfr90 ligands may be selected from the group 2-Methyl-4-Propyl-1,3-Oxathiane (MPOT), Cinnamaldehyde, Lyral, Allylbenzene, or combinations thereof. It is even more preferable that an Olfr90 ligand is selected from the group consisting of 1-Octen-3-ol (fungal); 2-Methyl-4-propyl-1,3-oxatiane; 2-Pentylfuran (fungal); Allylbenzene; Cinnamaldehyde; 2-Octanone (fungal); 3-Octanol (fungal); Benzyl Cyanide (fungal); Linalool (fungal).

Another embodiment of the present invention is a method of treating or preventing declining renal function in a subject comprising administering to the subject an effective amount of an Olfr90 ligand, salt, solvate, or stereoisomer thereof. It is preferable that an Olfr90 ligand is a fungal metabolite selected from the group consisting of 1-Octen-3-ol, 2-Pentylfuran, 1-Octen-3-one, 1,3-Dimethoxybenzene, Linalool, BenzylCyanide, 2-Octen-1-ol, 3-Octanol, 2-Octanone, 3-Octanone, 2-Octen-1-al, 1-octanol, 2,5-dimethylfuran, or combinations thereof. Other examples of Olfr90 ligands may be selected from the group 2-Methyl-4-Propyl-1,3-Oxathiane (MPOT), Cinnamaldehyde, Lyral, Allylbenzene, or combinations thereof. After administering to the subject an effective amount of an Olfr90 ligand, the subject preferably has an increased glomerular filtration rate when compared to the subject's glomerular filtration rate when the subject is not administered an Olfr90 ligand.

Another embodiment of the present invention is a method of identification of a fungal metabolite in a subject comprising: isolation of biological material; providing an Olfr90 or the ligand binding part thereof; placing the biological material in contact with Olfr90 or the ligand binding part thereof, and detecting the presence or absence of an Olfr90 ligand in the sample. The biological material is preferably blood or urine. This method preferably includes an additional step of quantifying the amount of Olfr90 ligand in the sample typically by the use of a computer that measures the detection (color, calcium influx, for example) corresponding to the amount of Olfr90 ligand in a sample. The methods of detecting Olfr90 ligand are described above and in the specification. These methods may be very beneficial as diagnostics in situations where subjects have toxic exposure to fungal contaminants.

Another embodiment of the present invention is a detection method comprising the following steps: providing a sample taken from a source to be tested for the presence of an Olfr90 ligand; placing the sample in contact with gas sensor comprising gold nanoparticle decorated, multi-walled carbon nanotubes; and detecting the presence or absence of an Olfr90 ligand in the sample.

DETAILED DESCRIPTION OF THE INVENTION

Olfactory receptors (ORs) are G protein-coupled receptors (GPCRs) which serve as chemosensors to detect odorants in the olfactory epithelium of the nose. Recently, ORs and other chemoreceptors have been found to play important roles in other areas of physiology, where they often serve as highly selective chemoreceptors in non-sensory tissues. These ORs and their downstream signaling machinery have also been found in the kidney. As a key regulator of homeostasis, the kidney carefully monitors the chemical composition of the forming urine as well as the plasma. The renal chemosensors could play an important role in aiding the homeostatic functions of the kidney. In fact, it was previously shown that mice lacking a downstream effector of OR signaling (adenylate cyclase 3) have defects in the regulation of both glomerular filtration rate and plasma renin, and that mice null for an individual renal OR (Olfr78) had renal based hypotension.

The present invention focuses on one OR, Olfr90, which was reported to be expressed both in murine kidney and in a macula densa cell line. When Olfr90 was identified as a renal OR in 2009, this receptor was an orphaned receptor (having no known activator molecule, i.e. ligand). Olfr90 fails to be delivered to the cell surface (i.e. traffic) in vitro making it hard to attempt deorphanization (all in vitro ligand assays for ORs require surface expression). In fact, the great majority of ORs are unable to reach the cell surface in vitro, and therefore identifying ligands is often prohibitively difficult. The present invention used a unique N-terminal tag which allows for surface trafficking of ORs in vitro, including Olfr90. This tag not only allowed Olfr90 to be targeted to the plasma membrane, but is cleaved off of the full-length protein after processing—therefore, the mature Olfr90 protein being studied does not have an additional tag which could alter ligand binding. The inventors of the present invention successfully deorphanized Olfr90 and have determined its ligands. Surprisingly, Olfr90 responded to (was activated by) a number of chemicals known to be fungal metabolites, including a metabolite known to be detected in patients with mold (e.g. *Aspergillus*) infections. The data of the present invention implies that renal sensory receptors may be interacting with metabolites from fungal sources as well. It is important to note that humans are constantly inhaling or ingesting fungi or fungal products, but only immunocompromised patients tend to become infected with these organisms The present invention demonstrates that pathways do exist to facilitate the detection of fungi or fungal byproducts (metabolites) in healthy individuals and that mammalian orthologs of Olfr90, such as mouse and human orthologs, are likely to act as sensors for fungal metabolites.

Identification of Physiologically Relevant Ligands which Activate Olfr90 and its Human Ortholog.

Seventeen ligands, of which 9 are most preferred, for Olfr90 were identified in the present invention, a human ortholog of Olfr90 (OR2H2) was expressed and cloned to identify evolutionarily conserved ligands.

Sensory Receptors in 'Non-Sensory' Tissues

Olfactory receptors (ORs) are seven transmembrane domain G-protein coupled chemoreceptors (GPCRs) which are encoded by ~1000 genes in the mouse and ~350 in humans, making them the largest gene family in the genome. In the nose, ORs are chemoreceptors used to detect odors by recognizing a wide variety of small molecular weight compounds. Recently, these chemoreceptors have also been found in tissues outside the nose, where they have a variety of different functions. For example, ORs play a role in sperm chemotaxis as well as in muscle adhesion and regeneration. The olfactory G protein ($G_{olfactory}$, or $G_{olf}$) and the olfactory form of adenylate cyclase (AC3) have been reported to co-localize in the kidney, and play a role in regulating renal function. A subset of ORs has also been found in the kidney, and an individual OR (Olfr78) has been reported to localize to the renal afferent arteriole, where it acts to modulate renin secretion and, ultimately, blood pressure. Intriguingly, the activator molecules (i.e. ligands) for Olfr78 have been found to be short chain fatty acids produced by commensal (symbiotic) gut microbiota. The gut microbiota produce these short chain fatty acids as a byproduct of their metabolism, and these compounds are then absorbed into the bloodstream of the "host." The present invention resulted in the elucidation of the role of another renal OR, Olfr90, in renal function.

Olfr90 and Ligand Identification

Figure 1:
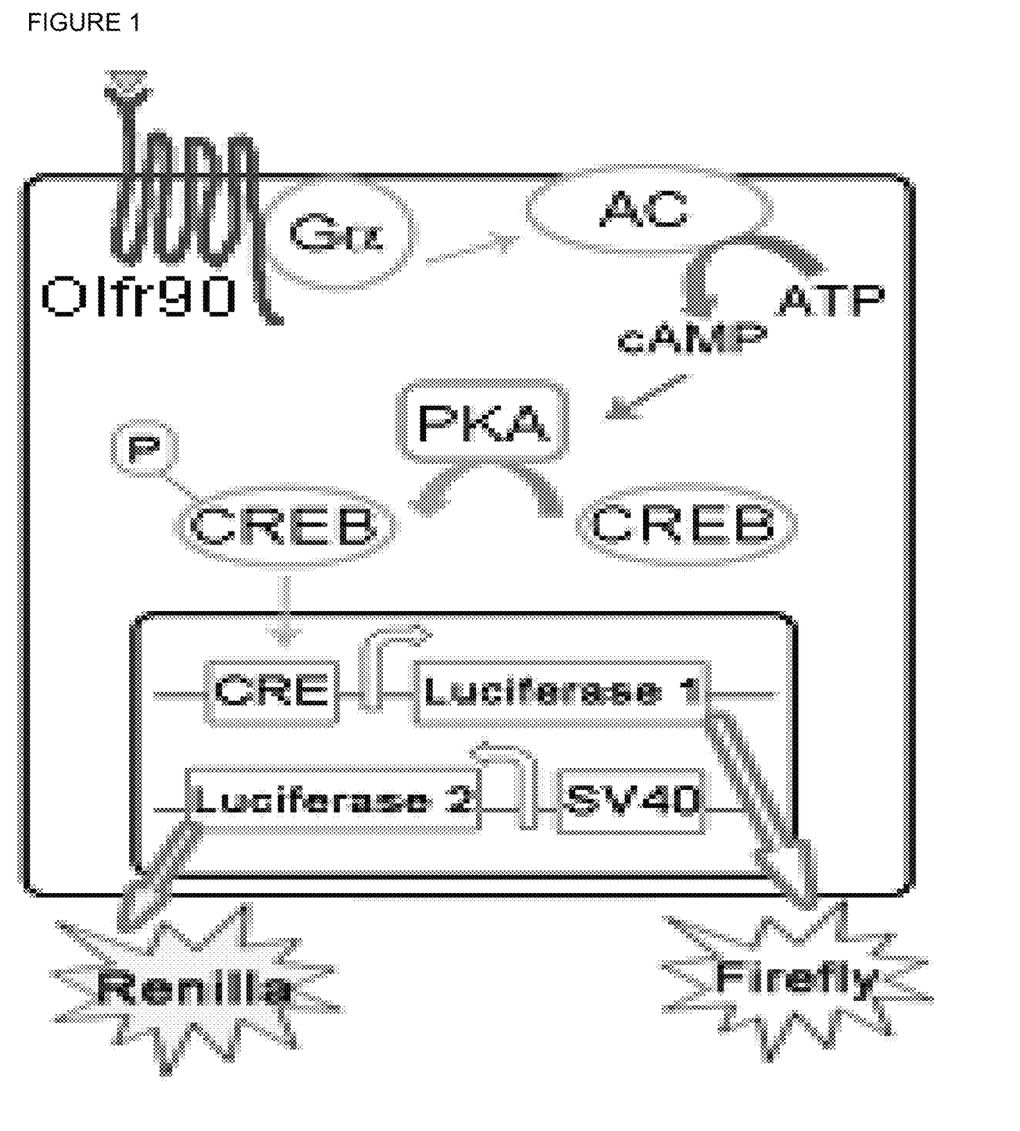
FIG. 1 illustrates the Luciferase Reporter Assay. HEK293T cells were transfected with Lucy-Olfr90 and two luciferase constructs, one of which was constitutively active (Renilla) while the other was only activated by an increase in intracellular cyclic AMP due to ligand binding (Firefly).

The full-length clone of Olfr90 from the kidney was found to be identical to the Olfr90 sequence found in the nose. As mentioned, Olfr90 was an orphan receptor with no known ligand. By identifying the ligands for this OR, the present invention has provided a key and necessary step in unraveling the physiological role that Olfr90 plays in the kidney. A luciferase reporter assay was employed for ligand screening (FIG. 1). In this assay, Olfr90 may be transfected into HEK293T cells along with a firefly luciferase construct whose activity is dependent upon elevated $[cAMP]_i$. Upon binding its ligand, the expressed Olfr90 increases $[cAMP]_i$, leading to increased transcription of firefly luciferase (FIG. 1). A constitutively active luciferase (Renilla) is co-transfected; therefore, the ratio of Firefly/Renilla is a measure of OR activation.

In this assay, it is essential that the Olfr90 is on the cell surface. Although Olfr90 is found on the cell surface in vivo, Olfr90 fails to traffic to the cell surface when heterologously expressed, regardless of the cell type used (COS cells, HEK cells, *Xenopus* oocytes, etc.). This is partly the reason why—despite screening systems such as the aforementioned luciferase assay—Olfr90 has remained an orphan receptor. A novel N-terminal tag which allows for surface trafficking of the majority of the renal Olfr90 was used. This tag is a leucine rich 17 amino acid sequence ("Lucy" tag) that not only aids in trafficking to the surface, but is cleaved before the Olfr90 reaches the cell surface. With the aid of the Lucy tag, a Flag tag (for detection purposes), and the chaperone protein Receptor-Transporting Protein 1 (RTP1S), the ligand profile of Olfr90 was determined.

Preliminary Data: Olfr90 Ligands

Olfr90 ligands that activate an Olfr90 protein were identified by testing mixes of chemicals with like properties (thiols mix, ketones mix, etc.) using the assay described above. These mixes have been used to screen ORs, and activate about 70% of olfactory sensory neurons. However, Olfr90 did not respond to any of these mixes. Next, Olfr90 was screened against ligands from ORs in the same genomic subfamily. ORs are the largest gene family in the genome, and are divided into subfamilies. Often, ORs within a subfamily (sibling ORs) share ligands in common. Olfr90 is a member of the MOR256 subfamily, which contains 37 genes. Of these 37 receptors, 6 have known ligands both published and unpublished for a total of roughly 121 ligands. We screened Olfr90 for responses to the six odorants which had been shown to activate 2 or more MOR256 family members, and found that Olfr90 responded to 2 odorants (Table 1, 3, and 5). Yet another strategy to identify ligands was to analyze a list of over 100 sibling ligands to discern which ligands were physiologically relevant. Using the Human Metabolomics Database (HMDB), it was determined which of the 'sibling ligands' were detected in either blood or urine, yielding an additional 30 chemicals for screening, 4 of which activated Olfr90. The 8 chemicals in HMDB classified as "odorants" found in human biofluids (blood, urine, saliva, or cerebrospinal fluid) was also tested, 3 of which activated Olfr90. In total, it was discovered that Olfr90 responded to 7 out of 38 potential ligands. Doses for testing were chosen based on published studies, experimentation, and/or concentrations reported in the HMDB.

In sum, as a result of these 3 strategies, 9 ligands which produced a reproducible and dose-dependent response from Olfr90 were discovered (Table 1). The remaining 77 ligands did not elicit a response, and no ligand tested elicited a response from an unrelated control OR. 7 of the 9 ligands have been reported in biofluids (Table 1), but only one is a known human metabolite. The inventors discovered that 4 of the 9 Olfr90 ligands (including the strongest ligand) were metabolites common to many species of fungus, including edible fungus (hence the appearance in the HMDB).

Figure 2:
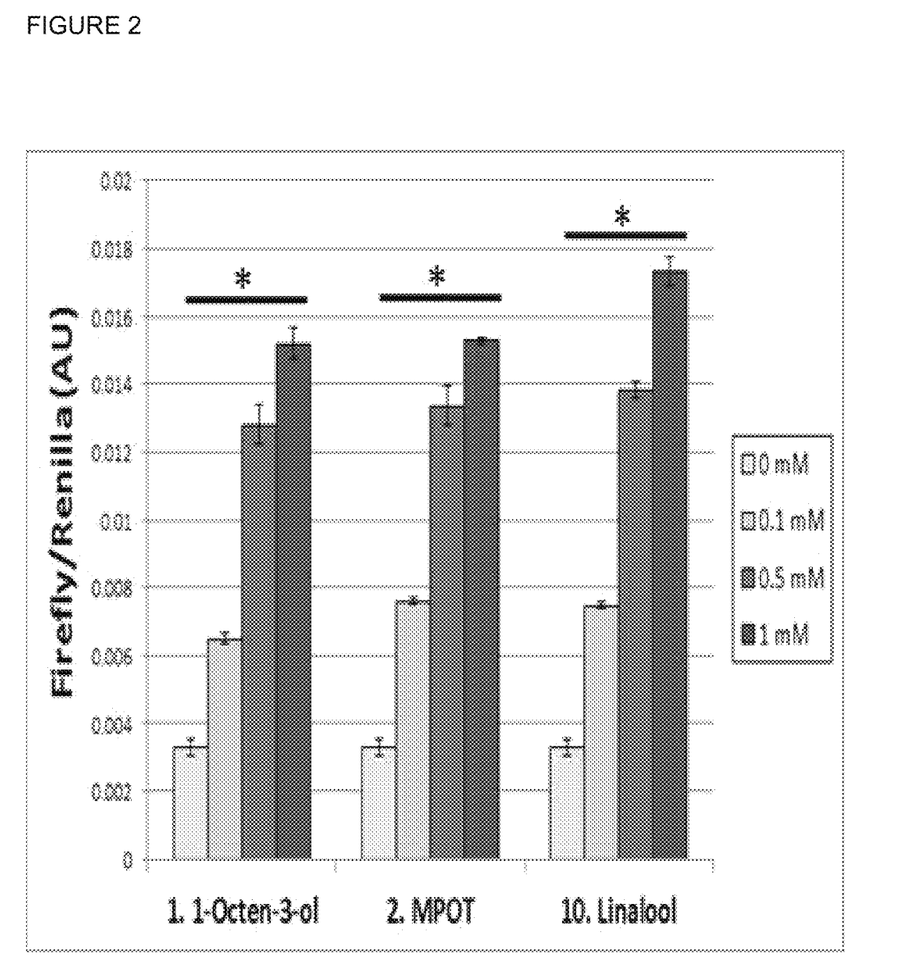
FIG. 2 illustrates Luciferase Output of the top 3 ligands for Olfr90. Olfr90 responded in a dose dependent manner to 1-Octen-3-ol, 2-Methyl-4-Propyl-1,3-Oxathiane (MPOT), and Linalool. (* indicates $p<0.0005$ for all conditions as compared to 0 mM).

To determine whether Olfr90 might be generally reactive to fungal metabolites, a list of common fungal metabolites from the literature was compiled and a subset of 13 chemicals (Sigma) was ordered. 7 of the 13 chemicals tested elicited a dose dependent response from Olfr90 (Table 2), but none activated an unrelated OR. Fungal metabolites are the strongest ligands for Olfr90 (FIG. 2), implying that Olfr90 may act as a renal sensor for fungal metabolites. Chemicals (Tables 1 & 2) reported to be present in biofluids in HMBD were not quantified so the exact physiological concentrations are not known. However, metabolites that are produced by molds growing in a filamentous (hyphal) stage, such as gliotoxin and aflatoxin are known to produce cellular apoptosis and long-term toxicities such as cancer. Other VOCs that are produced in the phase during asexual sporulation and recognized by Olfr90 (1-Octen-3-ol) are associated with the physiologic effects of "sick building syndrome". One Olfr90 ligand (2-Pentylfuran, Table 1 #7) is elevated in the breath of patients with *Aspergillus* infection. It is possible that a renal fungal metabolite sensor may be involved in regulating renal clearance of potentially toxic compounds produced by these fungi that are found in the airway and the gastrointestinal tract.

TABLE 1

Olfr90 ligands. Biofluid detection and natural sources of Olfr90 ligands identified in the initial set of screening, listed from strongest to weakest.

| | Odorant | Biofluids? | Source |
| --- | --- | --- | --- |
| 1 | 1-Octen-3-ol | + | Fungal |
| 2 | 2-Methyl-4-Propyl-3,1-Oxathiane (MPOT) | + | Plant |
| 3 | Cinnamaldehyde | + | Plant |
| 4 | 1-Octanol | + | Endogenous |
| 5 | Lyral | − | Artificial |
| 6 | Allylbenzene | − | Artificial |
| 7 | 2-Pentylfuran | + | Fungal |
| 8 | 1-Octen-3-one | + | Fungal |
| 9 | 1,3-Dimethoxybenzene | + | Fungal |

TABLE 2

Olfr90 ligands. Common fungal metabolites are Olfr90 ligands, listed from strongest to weakest.

| | Odorant | Biofluids? | Source |
| --- | --- | --- | --- |
| 10 | Linalool | + | Fungal |
| 11 | Benzyl Cyanide | + | Fungal |
| 12 | 2-Octen-1-ol | + | Fungal |
| 13 | 3-Octanol | + | Fungal |
| 14 | 2-Octanone | + | Fungal |
| 15 | 3-Octanone | + | Fungal |
| 16 | 2-Octen-1-al | + | Fungal |
| 17 | 2,5-Dimethylfuran | + | Fungal |

Determine if Olfr90 Respond to Media from Fungal Growth Cultures.

Figure 3:
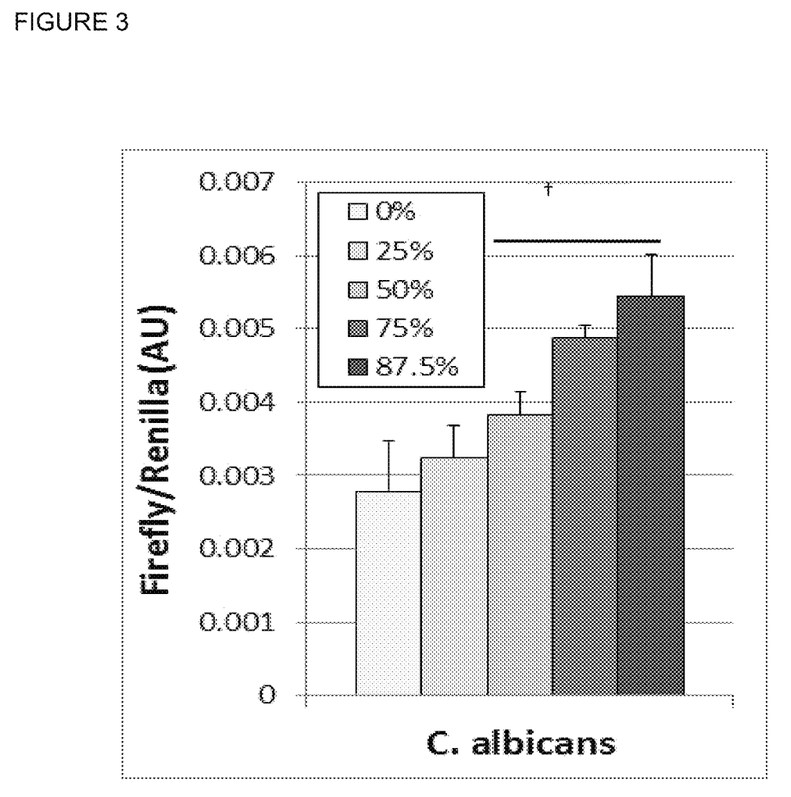
FIG. 3 illustrates Olfr90 responded to fungal metabolites in vitro. Olfr90 (but not any other OR tested) responded in a dose dependent manner to fungal growth media, but not to sterile Olfr90 (not shown, † is $p<0.05$ as compared to 0%).
Figure 4:
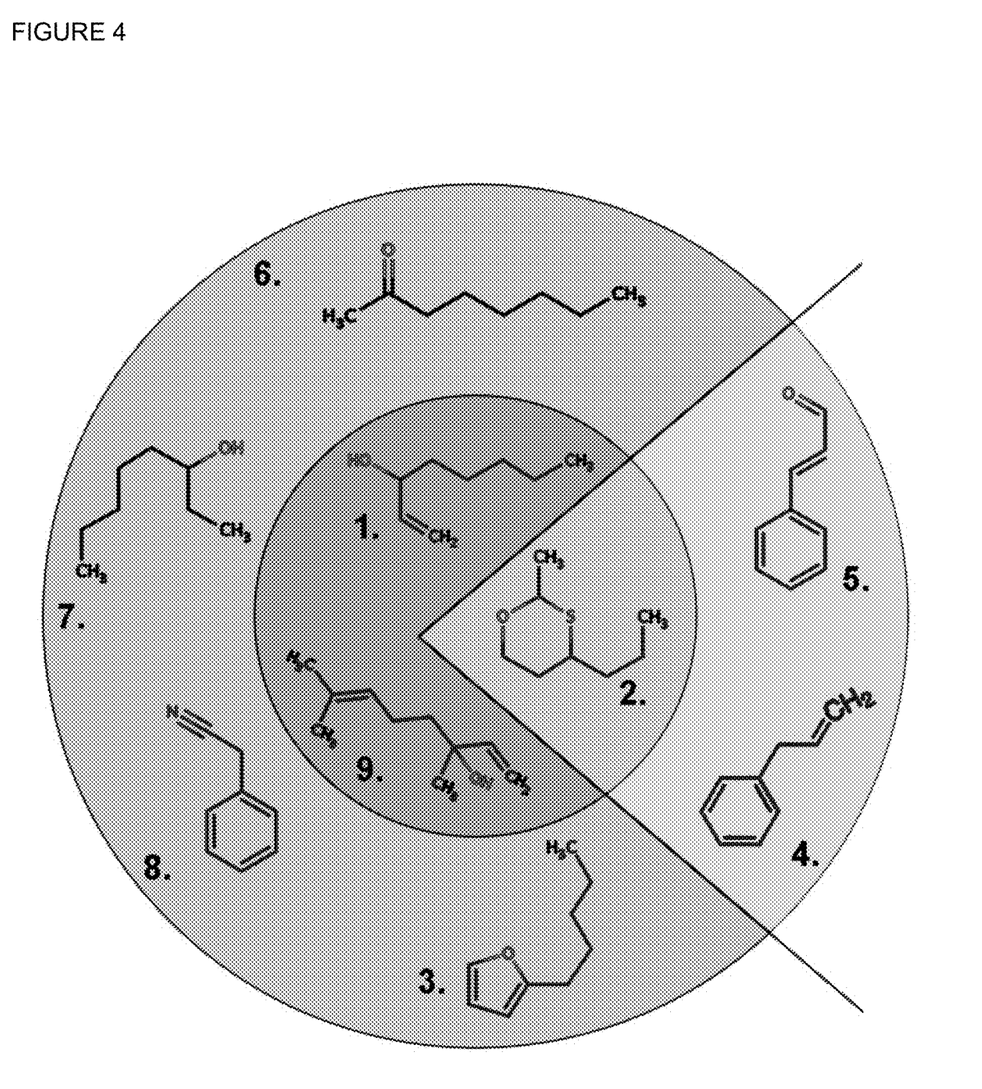
FIG. 4 illustrates the preferable ligands of Olfr90 for use in this invention. These are: 1-Octen-3-ol (#1); 2-Methyl-4-propyl-1,3-oxatiane (#2); 2-Pentylfuran (#3); Allylbenzene (#4); Cinnamaldehyde (#5); 2-Octanone (#6); 3-Octanol (#7); Benzyl Cyanide (#8); Linalool (#9). The "best" ligands are shown in the center ring. The shaded wedge of the circle (#2, 4, and 5) are non-fungal ligands; all other ligands are fungal in origin.
Figure 5:
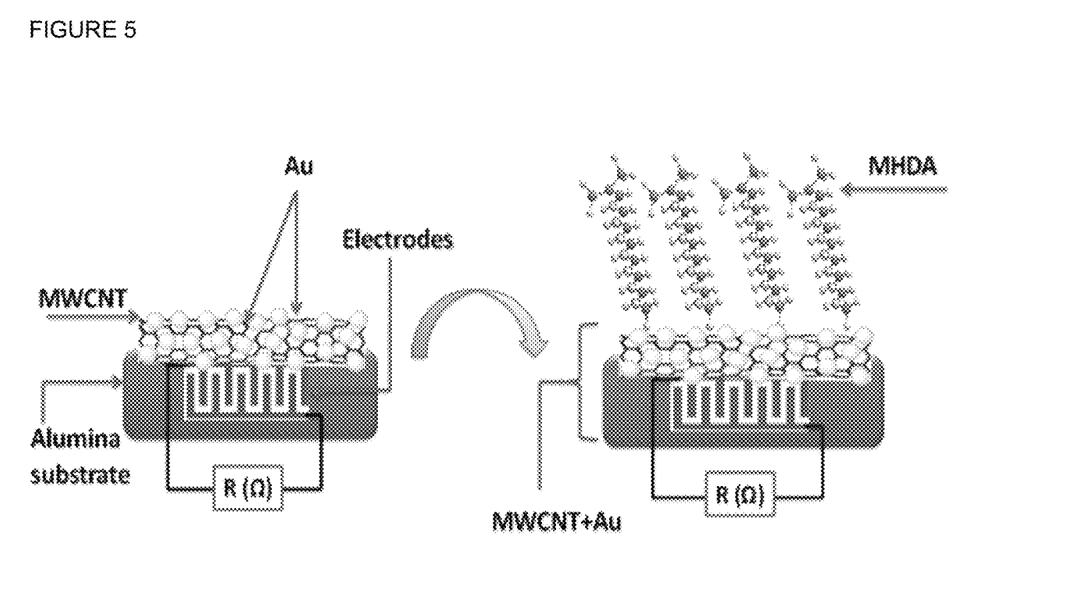
FIG. 5 illustrates an Olfr90 ligand gas sensor employing films of gold nanoparticles decorated, multiwalled carbon nanotubes (MWCNT/Au) functionalized with a self-assembled monolayer of 16 Mercaptohexadecanoic acid (MHDA). Please see a Nature Scientific Report article titled, "MHDA-Functionalized Multiwall Carbon Nanotubes for Detecting non-aromatic VOCs" written by Atef Tharri, Hamdi Baccar, Claudia Struzzi, Carla Bittencourt, Adnane Abdelghani & Eduard Llobet, published Oct. 10, 2016 (Scientific Reports [6:35130] DOI:10.1038/srep35130).

The data of the present invention showed Olfr90 is responsive to chemicals known to be common fungal metabolites. Because it was discovered that Olfr90 responds to isolated fungal metabolites, the inventors believed that it would also respond to media from fungal growth cultures (but not sterile fungal media). To pursue this, media from *Aspergillus fumigatus Candida* growth cultures were screened for the ability to activate Olfr90 in the luciferase assay. In brief, the fungi was grown for 24 hours in corked flasks in standard fungal media, pelleted by centrifugation, and the supernatant was filtered. As a control, sterile fungal culture media (without any fungal growth) was also used. The supernatants from these cultures were then added at varied doses to the luciferase assay as potential ligands' for Olfr90, and (as controls) an OR from the same subfamily (Olfr1393) and from a different subfamily (Olfr78). If Olfr90 is indeed responding to fungal metabolites, the inventors expected to find that supernatant from fungal cultures (but not sterile media without exposure to fungal growth) will activate Olfr90. Indeed, as shown in FIG. 3, the inventors discovered that Olfr90 responded in a dose dependent manner to media in which *Aspergillus fumigatus* was cultured, but not sterile media, suggesting that the metabolites produced by *Aspergillus fumigatus* in culture are Olfr90 ligands. The dose-response seen with Olfr90 was absent with Olfr1393 and Olfr78, indicating the specificity of the response. Based on this data, it is believed that fungal metabolites are ligands for Olfr90.

Figure 6:
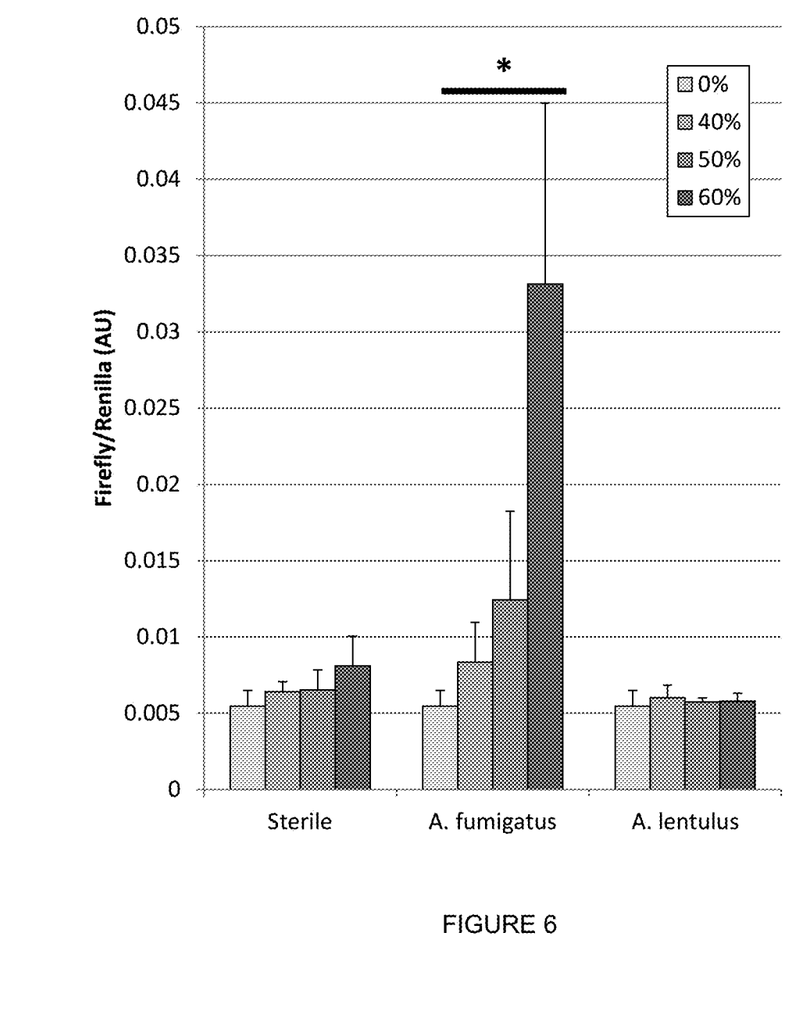
FIG. 6 illustrates Olfr90 responds to fungal metabolites. Olfr90 exhibits a dose-dependent response to *A. fumigatus* but not *A. lentulus*. An unrelated OR, tested as control, did not respond (not shown).

As illustrated in FIG. 6, both *Aspergillus fumigatus* and the related, but metabolically disparate *Aspergillus lentulus* were grown in culture media, using conditions conducive for secondary metabolite production. Harvested media, and sterile (control) media were then tested for their abilities to activate Olfr90. Olfr90 responded to the "*A. fumigatus* media," but not sterile media or the *A. lentulus* sample in the luciferase assay. This was particularly intriguing because *A. fumigatus* is a common human colonizer and pathogen that produces different metabolites compared to *A. lentulus*, which is an atypical cause of human disease but a more prevalent organism in the environment. Thus, it is an extremely exciting development that Olfr90 appears to not only detect the hallmarks of fungal presence, but in particular detects the products of particular disease-causing fungi.

Diagnostic Applications

Diagnostic applications of this technology include:
(1) Air/Environmental Monitoring
a. For example, air samples or physical environmental samples (walls scrapings, drywall, etc.) could be tested for Olfr90 ligands as an index of fungal presence. This could involve a filter to collect samples from the air, or could involve taking a solid sample (drywall, etc.) and homogenizing it in a liquid. This would allow for a laboratory-based test of the present invention, described below, to identify the most common contaminates that produce Olfr90 ligands involved in environmental toxicities, such as with 'sick building syndrome'.

(2) Food, Water, Product Spoilage a. Testing of food, water, or fluid samples could identify the presence of Olfr90 ligands. Testing for the presence of Olfr90 ligands in bread, grains, wine, water, etc. samples would allow for a laboratory-based tests of the present invention to identify the presence of compounds most frequently associated with food and product spoilage.

(3) Testing of Medical Samples a. Testing of samples obtained from patients could serve as a diagnostic tool to identify pathogenic fungi involved in both allergic and invasive syndromes. For example, blood, serum, urine, respiratory samples, breath, bronchoalveolar lavage, or sputum could be tested in order to detect Olfr90 ligands that are implicated in asthma, fungal sinusitis, allergic bronchopulmonary sinusitis, and invasive fungal pneumonia using the methods of the present invention.

Assays of the Present Invention

Assays using Olfr90 as a diagnostic are outlined below. These include use of whole-cell assays and in vitro assays. One can envision using cellular models in a cassette type of format, or plate format, in which a solute such as tissue homogenate, or product homogenate is incubated on the cells for a certain amount of time before the read-out is interpreted. One can also envision a method, or model, in which these cells are directly exposed to measured volumes of air, using environmental air sampling container or breath-sampler is used to expose cells to airway breath. Then the presence and the amount of one or more ligands that bind to Olfr90 will be identified, analyzed and/or quantified.

Binding/Expression Assays

A sample obtained from (1) air/environmental monitoring, (2) food water product spoilage, (3) from subjects as described above may be analyzed using one or more binding/expression assays described below as examples. If an Olfr90 ligand, such as one or more of the ligands described in Tables 1 and 2, is present in a sample, then this Olfr90 ligand will bind to an Olfr90 protein, preferably a mammalian protein such as human or mouse, and be displayed by the assay indicating fungal growth, infection, or contamination within the sample.

CA2+ Assay

In the HEK cell model, cells are co-transfected with Olfr90 along with a G protein that couples OR activation to calcium signaling (i.e., $G_{alpha}15/16$), thereby coupling the OR activation pathway to the $IP_3$ pathway and release of calcium stores[2][3]. Olfr90 may be transfected with or without various chaperones (Ric8b, RTP1S, REEP, etc.) and with or without various tags (Rho, Flag, Lucy, etc.). Odorant binding will be determined by increases in intracellular $[Ca^{2+}]$ as measured by Fura-2. In brief, for these experiments HEK-293T cells will be plated onto coverslips, and will be transfected (using Lipofectamine) with a Flag-tagged OR together with $G_{alpha}15/16$ (a G protein which couples OR activation to the $IP_3$ pathway and calcium store release). 1-2 days post-transfection, the cells will be incubated for 60-90 minutes in HEK Ringer's containing 7 uM Fura-2 (Fura 2-AM), 0.09 g/dl DMSO and 0.018 g/dl Pluronic F-127 (Molecular Probes, Eugene, Oreg.)[4]. Calibration of the Fura-2 signal will be performed as previously described[4]. Cells will then be imaged in HEK Ringer's, applying 1 mM of odorant mix (rate of 50 uL/sec over 20 sec), with images being captured at a rate of 20× every 4 sec, for a total of 4-5 minutes. Once the response returns to baseline, a subsequent odorant response will be tested, for a maximum imaging time of 1.5-2 hr per coverslip. At the end of the experiment, 10 uM ATP is given to verify cell viability.

Chloride Current Assay

For the oocyte experiments, *Xenopus laevis* oocytes will be injected with an OR of interest along with $G_{olf}$ and CFTR (cystic fibrosis transmembrane conductance regulator). Olfr90 may be introduced with or without various chaperones (Ric8b, RTP1S, REEP, etc.) and with or without various tags (Rho, Flag, Lucy, etc.). For this assay, the readout is cAMP-activated CFTR current[3][5]. Similar to protocols described previously[5], oocytes will be harvested from mature female *Xenopus laevis*. After treatment with collagenase type I (1 hr, room temperature), mature, healthy oocytes will be selected for cRNA injection. Injected oocytes will be incubated at 18° C. in fresh Barth's solution. After 3-4 days, two-electrode voltage clamp recordings of injected oocytes will be performed at a holding potential of −80 mV.

Luciferase Assay

In HEK cells or hana3 cells, Olfr90 will be expressed along with along with a firefly luciferase construct whose activity is dependent upon elevated $[cAMP]_i$. Olfr90 may be transfected with or without various chaperones (Ric8b, RTP1S, REEP, etc.) and with or without various tags (Rho, Flag, Lucy, etc.). Upon binding its ligand, the expressed OR increases $[cAMP]_i$, leading to increased transcription of firefly luciferase. A constitutively active luciferase (Renilla) is co-transfected; therefore, the ratio of Firefly/Renilla is a measure of OR activation. (This is shown in FIG. 1).

HELA/OLF System

Olfr90 may be transfected with or without various chaperones (Ric8b, RTP1S, REEP, etc.) and with or without various tags (Rho, Flag, Lucy, etc.). This system is similar to the luciferase assay but differs in the readout—here, Olfr90 activates an exogenously expressed CNG channel (CNGA2). When cAMP binds to CNGA2, the calcium influx can be measured via a calcium sensitive dye or with a FLIPR assays. (This is panel C in figure below).

Other Assays

The inventor envisions construction of non-cellular methods that could be employed in both the environmental applications (1, described above), food applications (2, described above)] and clinical diagnostic applications (3, described above). This can include:

(a) Reporter-Displacement

Immobilized olfr90 or a smaller relevant piece (ligand binding pocket or "functional domain" or an aptamer representing such functional domain would be pre-bound with both a reporter fluorophore (and a tag of some type) and a quencher (which blocks signal from the tag). In fact, perhaps the olfr90 itself can be chemically modified to include the quencher. Assuming that ligand binding to Olfr90 is competitive, binding of the ligand to Olfr90 should displace the reporter containing molecule; as the distance of the reporter-fluorophore from the quencher increases, detectable fluorescence signal would also increase.

(b) Competitive Inhibition Binding Assay

Olfr90 or a smaller relevant piece of olfr90 (i.e., functional binding pocket) is immobilized. First, the sample of interest is exposed to the immobilized Olfr90 and allowed to bind. Subsequently, a labeled ligand is added (which can only bind to Olfr90 that did NOT bind to anything in the sample of interest). The amount of labeled ligand that binds is inversely proportional to the amount of ligand in the sample of interest. Label could be fluorescent, colorimetric/ absorbance, etc. Instead of a labeled ligand, one could also use a labeled antibody that can only bind if no ligand is bound.

(c) Binding Assay

The sample of interest is immobilized. The sample of interest is then exposed to a small protein/aptamer representing olfr90 or the critical binding pocket of Olfr90 which is labeled with some fluorophore or tag. The amount of fluorophore or tag which remains bound to the sample surface (which can then be measured) is indicative of the amount of Olfr90 ligand present.

(d) Dipstick

Recombinant protein (i.e., aptamer or small part of Olfr90) is immobilized on a strip (i.e., dipstick), Theoretically, any assay that can be reduced to an ELISA format can then be further reduced to a dipstick format, in which the receptor is immobilized, and the ligand moves through the solvent phase to interact with the receptor to initiate downstream signal generation.

Olfr90 Ligands as Therapeutic Agents

As mentioned, data[1] indicates that Olfr90 may localize to the 'macula densa' of the kidney. The macula densa acts as a sensor to precisely control glomerular filtration rate (GFR) on a single nephron level. The inventors believe that Olfr90 in the macula densa may act to increase GFR in response to a fungal infection in order to facilitate clearance. Therefore, if macula densa Olfr90 is activated in a patient without a fungal infection, it would be expected that it would increase GFR. Thus, activating Olfr90 is a potential therapeutic to increase GFR—i.e., in patients with declining renal function, or even with people in which renal clearance is needed, such as in the case of toxic exposures of drugs or other toxins. This could be accomplished by treating a patient with (a) one of the existing Olfr90 ligands described herein, or, (b) with a similar compound with low toxicity, in order to increase the levels of ligand that reach the renal macula densa.

Pharmaceutical compositions of the present invention comprise an effective amount of one or more of Olfr90 ligands, such as one or more of the 17 ligands described in Tables 1 & 2, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one Olfr90 ligand or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

An Olfr90 ligand may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The Olfr90 ligand may be provided to the individual in need thereof by dietary ingesting one or more comestibles that comprise the Olf90 ligand, such as herbs, berries, and/or fruits.

The Olfr90 ligand may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include an Olfr90 ligand, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the Olfr90 ligand may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In one embodiment of the present disclosure, the Olfr90 ligands are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No.

5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, an Olfr90 ligand may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 67,537,514, 6,613,308, 5,466,468, 5,543,158; 5,641, 515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the active compound of an Olfr90 ligand may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, an Olfr90 ligand may be comprised in a kit.

The kits may comprise a suitably aliquoted Olfr90 ligand and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the Olfr90 ligand and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The Olfr90 ligand composition(s) may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

REFERENCES

1. Pluznick, J. L., et al. Functional expression of the olfactory signaling system in the kidney. Proc. Natl. Acad. Sci. U.S.A. 106, 2059-2064 (2009).
2. Kajiya, K., et al. Molecular bases of odor discrimination: Reconstitution of olfactory receptors that recognize overlapping sets of odorants. J Neurosci 21, 6018-6025 (2001).
3. Peterlin, Z., Firestein, S. & Rogers, M. E. The state of the art of odorant receptor deorphanization: a report from the orphanage. J Gen Physiol 143, 527-542 (2014).
4. Ma, R., Smith, S., Child, A., Carmines, P. K. & Sansom, S. C. Store-operated Ca(2+) channels in human glomerular mesangial cells. Am J Physiol Renal Physiol 278, F954-F961 (2000).
5. Katada, S., Nakagawa, T., Kataoka, H. & Touhara, K. Odorant response assays for a heterologously expressed olfactory receptor. Biochem. Biophys. Res. Commun 305, 964-969 (2003).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A detection method comprising the following steps:
   a) providing a sample taken from a source to be tested for the presence of a Olfr90 ligand;
   b) providing an Olfr90 or a ligand binding part thereof;
   c) placing the sample in contact with Olfr90 or the ligand binding part thereof; and
   d) detecting the presence or absence of an Olfr90 ligand in the sample, wherein the ligand binding part of Olfr90 binds to 1-Octen-3-ol; 2-Methyl-4-propyl-1,3-oxatiane; 2-Pentylfuran; Allylbenzene; Cinnamaldehyde; 2-Octanone; 3-Octanol; Benzyl Cyanide; Linalool or a combination thereof.

2. The method of claim 1, wherein the source may be air, water, food, soil, wall scrapings, blood, urine respiratory samples.

3. The method of claim 1 wherein the ligand binding part of Olfr90 is provided.

4. The method of claim 1, wherein the Olfr90 or the ligand binding part thereof is attached to a reporter and the detecting the present or absence of an Olfr90 ligand in the sample occurs by the displacement of the reporter if the Olfr90 ligand is present in the sample.

5. The method of claim 1 wherein Olfr90 or the ligand binding part thereof is expressed in eukaryotic cells along with a firefly luciferase whose activity is dependent upon elevated [c-AMP] whereby the detecting the presence or absence of an Olfr90 ligand occurs by binding of the Olfr90 ligand to the Olfr90 or ligand binding part thereof elevates the concentration of [cAMP] leading to increased transcription of firefly luciferase if an Olfr90 ligand is present in the sample.

6. The method of claim 1 wherein Olfr90 or the ligand binding part thereof is expressed in eukaryotic cells and a CNG channel (CNGA2) is expressed exogenously, whereby the detecting the presence or absence of an Olfr90 ligand occurs by binding of the Olfr90 ligand to the Olfr90 or ligand binding part thereof elevates the concentration of [cAMP] leading to increased cAMP binding to CNGA2 and a resulting calcium influx may be measured via a detector if an Olfr90 ligand is present in the sample.

7. The method of claim 6 wherein the detector is a calcium sensitive dye or a FLIPR assay.

8. The method of claim 1 wherein in step b) the ligand binding part of Olfr90 is provided and immobilized to a surface.

9. The method of claim 8 further comprising the steps:
   incubate the sample with the ligand binding part of Olfr90 to form a mixture; and
   add a Olfr90 ligand with a label.

10. The method of claim 9 wherein the label is selected from the group consisting of a fluorescent tag, colorimetric tag, or absorbance tag.

11. The method of claim 1 wherein in step b the ligand binding part of Olfr90 is an aptamer representing the binding site of Olfr90 and the aptamer is labeled with a tag.

12. The method of claim 11 wherein the tag is a fluorophore.

13. The method of claim 12 wherein the aptamer is attached to a surface.

14. The method of claim 13 wherein detecting the presence or absence of an Olfr90 ligand in the sample is determined by the amount of fluorophore that remains bound to the aptamer.

15. The method of claim 14 wherein the surface is a strip.

16. The method of claim 15 wherein the strip is a dip stick.

17. The method of claim 1 wherein the Olfr90 ligand is selected from the group 2-Methyl-4-Propyl-1,3-Oxathiane (MPOT), Cinnamaldehyde, Allybenzene, or combinations thereof.

* * * * *